United States Patent [19]

Kaiser

[11] 4,354,972

[45] Oct. 19, 1982

[54] SYNTHESIS OF STEROIDS

[76] Inventor: Emil T. Kaiser, 5634 S. Woodlawn Ave., Chicago, Ill. 60637

[21] Appl. No.: 291,435

[22] Filed: Aug. 10, 1981

Related U.S. Application Data

[63] Continuation-in-part of Ser. No. 236,160, Feb. 20, 1981, abandoned, and Ser. No. 278,838, Jun. 29, 1981.

[51] Int. Cl.$^3$ .............................................. C07J 71/00
[52] U.S. Cl. .................. 260/239.55 R; 260/239.55 C; 260/397.1; 260/397.3
[58] Field of Search .......... 260/397.1, 397.3, 239.55 C

[56] References Cited

U.S. PATENT DOCUMENTS 4,174,345  11/1979  Kaiser .............................. 260/397.1
4,217,279   8/1980  Kaiser .............................. 260/397.1

*Primary Examiner*—Elbert L. Roberts
*Attorney, Agent, or Firm*—Carl C. Batz

[57] ABSTRACT

This invention relates to the synthesis of steroids which are useful for their biological activity or which may be converted to steroids which have such activity. These syntheses include the steroid compounds and processes for their preparation.

An object of the invention is to provide syntheses which are applicable to materials which are readily available in good supply for converting such materials to steroids which are useful and desirable in the manufacture of pharmaceutical products.

More particularly, I have sought to discover processes and intermediate compounds useful in the synthesis of 24, 25-dihydroxycholesterol from hyodeoxycholic acid or lithocholic acid which are constituents of, and readily available from, animal bile.

24 Claims, No Drawings

SYNTHESIS OF STEROIDS

This application is a continuation-in-part of my application Ser. No. 236,160, filed Feb. 20, 1981 now abandoned and my application Ser. No. 278,838 filed June 29, 1981.

BACKGROUND

In my U.S. Pat. Nos. 4,134,905; 4,163,744; 4,174,345; 4,183,852 and 4,217,279, I describe syntheses for the preparation of 25-hydroxycholesterol and its derivatives from 24-carbon-24-alcohol steroids with protected 3- and 6-hydroxyl or ketone groups. Included in these syntheses is the extension of the side chain of the 24-carbon-24-alcohol steroid with a cyano group to a 25-carbon steroid.

Steroid aldehydes have been prepared by ozonization of dibromostigmasterol acetate to yield 3-acetoxy-bis 5-cholenaldehyde and from thiol esters of deoxycholic acid, 3$\beta$-hydroxy-5-cholenic and -bisnor-5-cholenic acid to yield the corresponding steroid aldehydes, by desulfurizing said thiol esters with Raney nickel. These procedures were described in the following publications: A. P. Certolella et al, JACS, 70, 2953 (1948); R. H. Levine et al, ibid, 70, 511 (1948); G. B. Spero et al, ibid, 70, 1907 (1948); and A. V. McIntosh et al, ibid, 70, 2955 (1948).

DISCLOSURE OF THE INVENTION

By the present invention, I now transform the 24-carbon-25-alcohol steroids into 24-carbon-24-aldehydes by procedures which do not oxidize the 24-position beyond the aldehyde stage and do not affect the protecting groups of the 3- and 6-functions. The 24-carbon steroid 24-aldehydes may be used as intermediates for the production of 24, 25-dihydroxycholecalciferol and 1, 24, 25-trihydroxycholecalciferol, hydroxylated vitamin $D_3$ useful for the treatment of calcium metabolism disorders.

Starting materials for the syntheses may be any of the 24-carbon-24-alcohol steroids derived from hyodeoxycholic acid or from lithocholic acid which may be prepared in accordance with procedures disclosed in my U.S. Pat. Nos. 4,134,904; 4,163,744; 4,174,345; 4,183,852 and 4,217,279. These 24-carbon-24-alcohol steroid starting materials include the following:

The 24-carbon-24-alcohol steroid having the structure:

Compound I

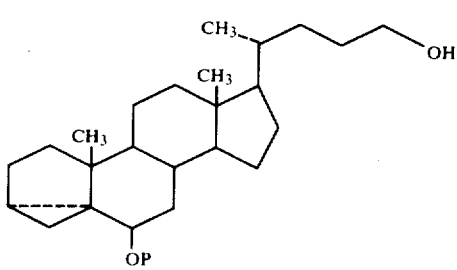

where P is an aliphatic group, such as a lower alkyl group, preferably methyl. (See U.S. Pat. No. 4,134,904.)

The 24-carbon-24-alcohol steroid having the structure:

Compound IIa

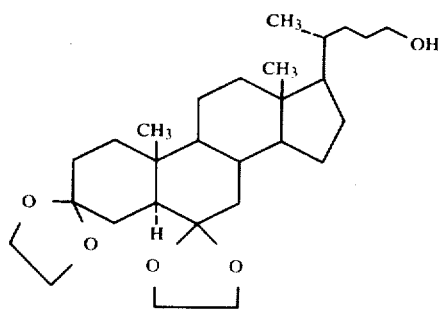

(See U.S. Pat. No. 4,163,744.)

The 24-carbon-24-alcohol steroid having the structure:

Compound IIb

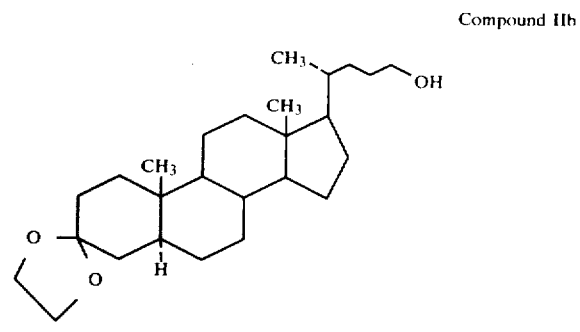

which compound may be prepared from lithocholic acid in the same manner and by the same procedure as is Compound IIa from hyodeoxycholic acid. (See U.S. Pat. No. 4,163,744.)

The 24-carbon-24-alcohol steroid having the structure:

Compound III

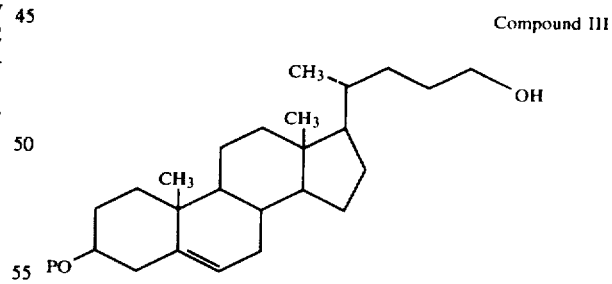

in which P is 2-tetrahydropyranyl (2-THP) or $\beta$-methoxyethoxymethyl (MEM). (See U.S. Pat. No. 4,183,852; or P may be tertiary-butyloxycarbonyl (t-Boc). (t-Boc-ethers may be prepared according to Rec. Trav. Chem., 81, (1962) or J. Amer. Chem. Soc., 85, 208 (1963) or Ann. 670, 127 (1963)); or P may be trimethylsilyl ($Me_3Si$) or tertiary-butyl dimethylsilyl ($Me_2$t-BuSi) (Process Biochemistry, 9 (1980)).

The 24-carbon-25-alcohol steroid which has the structure:

Compound IVa

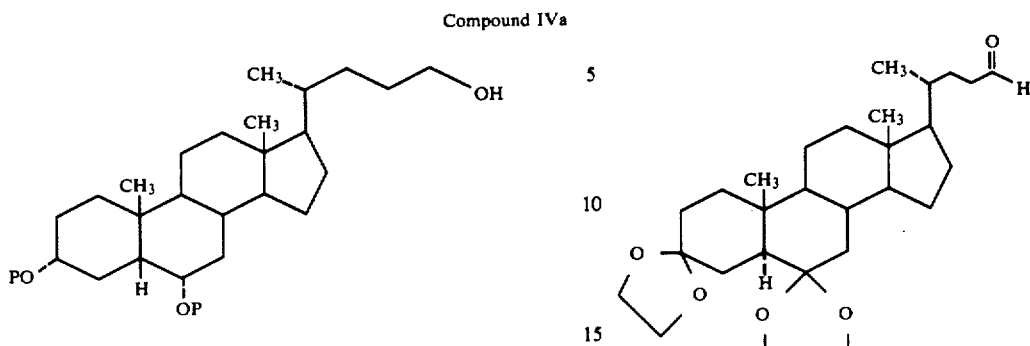

where P is 2-THP or β-methoxyethoxymethyl or P may be t-Boc or Me₃Si or t-BuMe₂Si. (See U.S. Pat. No. 4,217,279.)

The 24-carbon-25-alcohol steroid which has the structure:

Compound IVb

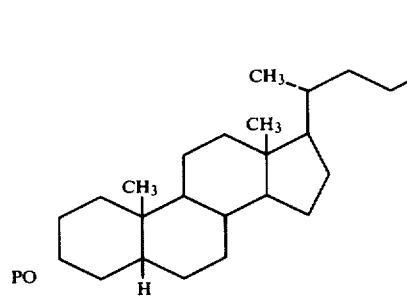

and which is prepared from lithocholic acid as in Compound IVa from hyodeoxycholic acid (See U.S. Pat. No. 4,217,279.) and in which P is the same as stated in Compound IVa.

The 24-carbon-24-alcohol steroids, of which the above mentioned Compounds I, IIa, IIb, III, IVa, and IVb are examples, may be oxidized to aldehydes according to procedures which do not affect the protecting groups in the 3- and 6-positions and do not oxidize the 24-hydroxyl beyond the 24-aldehyde stage.

Thus, Compound I becomes

Compound V

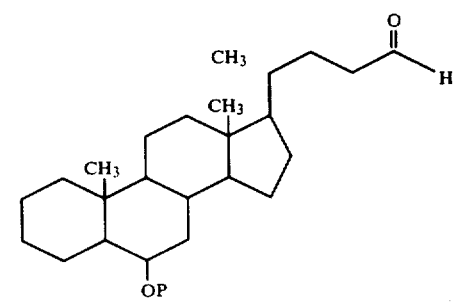

in which P is the same as in Compound I. Compound IIa becomes

Compound VIa

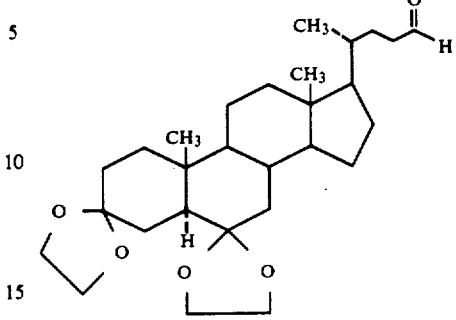

Compound IIb becomes

Compound VIb

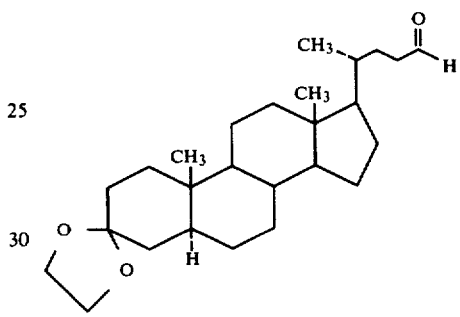

Compound III becomes

Compound VII

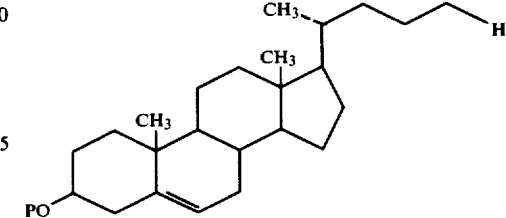

in which P is the same as in Compound III. Compound IVa becomes

Compound VIIIa

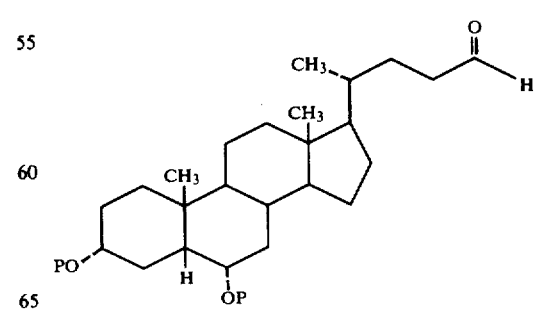

in which P is the same as in Compound IVa. Compound IVb becomes

Compound VIIIb

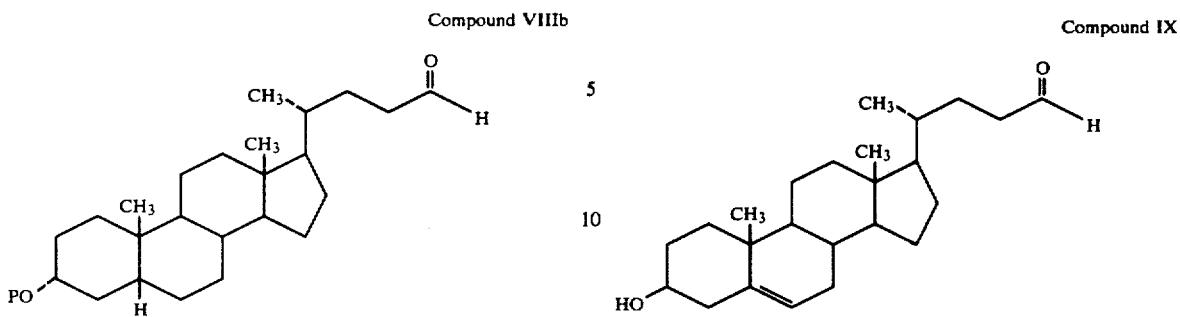

in which P is the same as in Compound IVa.

These steroids (represented by Compounds I, IIa, IIb, III, IVa or IVb) may be oxidized by any one of the following methods.

(A) Oxidation with chromium trioxide-pyridine complex, Org. Syn., 55, 84 (1976)

These steroid starting materials may be dissolved in methylene chloride and mixed with a solution in methylene chloride of the chromium trioride-pyridine complex. After a black tar adhering to the wall of the vessel settles, the methylene chloride solution is separated, washed, dried and evaporated under reduced pressure. The dry residue may be identified by nmr and ir data as the 24 aldehyde, of the starting steroid derivative.

(B) Oxidation by the Sulfoxide-arbodiimide reaction (J. Amer. Chem. Soc. 87 5670)

The steroid starting material may be dissolved in a mixture of dimethylsulfoxide and benzene or toluene, and pyridine and trifluoroacetic acid (2 moles pyridine for 1 mole trifluoroacetic acid) added. A solution of dicyclohexyl carbodiimide in ethyl acetate may then be added, and the mixture stirred until all the dicyclohexylurea has settled out. The insoluble dicyclohexylurea may be removed by filtration; and from the filtrate, the same aldehydes, with the same ir and nmr data, may be isolated as may be obtained by the chromium trioride-pyridine complex oxidation.

(C) Oppenauer oxidation, Org. Reactions, Volume VI, 207 (1961)

Aluminum isopropoxide may be dissolved in a previously dried mixture of toluene and cyclohexanone, and the steroid starting material may be added. After one to four hours of refluxing, the solution may be washed with water, dried and evaporated under reduced pressure. The residue may be identified by ir and nmr data as the aldehyde of the starting steroid derivative.

Thus, I have produced, for the first time, 24-carbon-24-aldehyde derivatives of hyodeoxycholic and lithocholic acid, which may be further converted to other steroids having biological activity. This conversion may begin with the removal of protective groups.

Removal of Protecting Groups

From the protected 24-aldehydes prepared by oxidation, using either of procedures A, B or C above outlined, we may obtain 24 aldehydes with 3-hydroxyl or ketone functions.

From Compound V, we obtain a steroid having the structure:

Compound IX

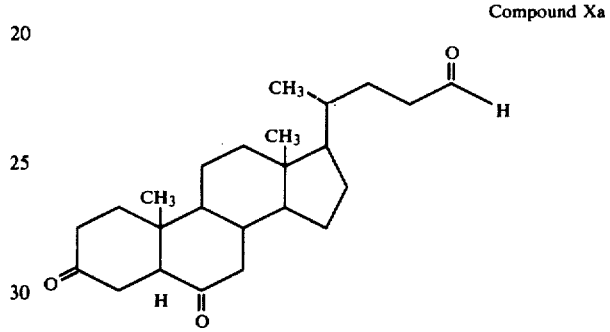

From Compound VIa, we obtain a steroid having the structure

Compound Xa

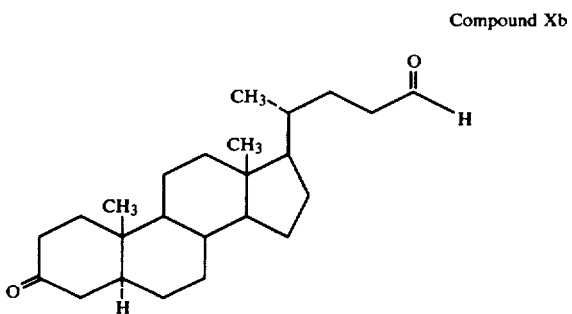

From Compound VIb, we obtain a steroid having the structure:

Compound Xb

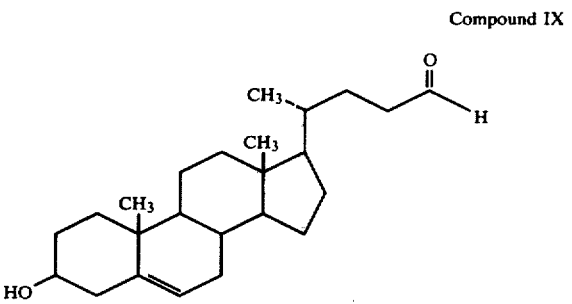

From Compound VII, we obtain a steroid having the structure:

Compound IX

From Compound VIIIa, we obtain a steroid having the structure

Compound XIa

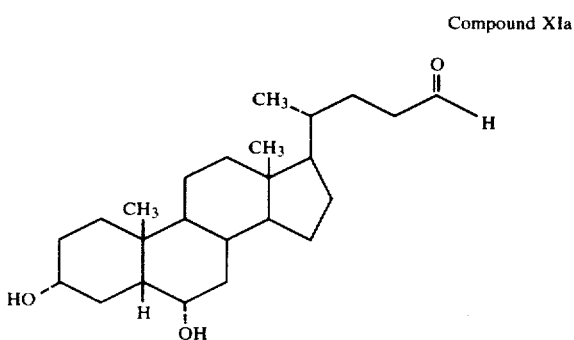

From Compound VIIIb, we obtain a steroid having the structure:

Compound XIb

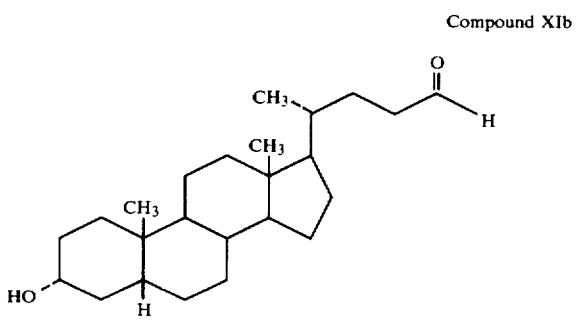

We obtain these Compounds IX, Xa, Xb, XIa and XIb by using the following hydrolytic procedures.

For compounds protected with the 3α, 5-cyclo group (i-steroid), 2-tetrahydropyranyl, t-butyloxycarbonyl, trimethylsilyl, and t-butyldimethylsilyl groups—Compounds V, VIa, VIb, VIIa, VIIIb—the protecting group removal may be carried out in the following manner:

The compound to be deprotected is refluxed in a mixture of water; and a water soluble alcohol, or of water and dioxane and 0.1 to 0.5% of an organic acid, such as p-toluenesulfonic acid or trifluoracetic acid, or an inorganic acid, such as sulfuric acid, until the protecting group removal is completed. By ir and nmr spectroecopy, it may be shown that the hydroxyl groups are restored, and the aldehyde groups remain unchanged. The resulting compounds are: Compound IX, Compound IXa and Compound XIb.

The dioxodiethylene group may be removed in a similar manner and keto steroid 24-aldehydes with structures Xa and Xb being obtained.

Removal of the β-methoxyethoxymethyl group occurs when Compound VII, VIIIa, or VIIIb, in which P is β-methoxyethoxymethyl dissolved in methylene chloride containing a 1 to 6 carbon alcohol in concentrations up to 5%; then zinc bromide is added, and the mixture stirred until the free hydroxyl groups are restored. The ir and nmr data show that the structures are as given for Compounds IX, XIa and XB, respectively, the same as the structures obtained by acid hydrolysis.

The steroid 24-aldehydes with 3- and 6-hydroxyl functions may be protected again with groups which are less sensitive to the acid hydrolysis. Particularly, steroids esterified with aliphatic carboxylic acids or aromatic carboxylic acids (see structures given below) where R is the alkyl acyl group or aromatic acyl group, are important intermediates in synthesis, in which new substituents are being introduced into the nucleus. Esterification techniques, such as reactions with acid anhydrides or with acid halides, in the presence of a base, may be used to produce 3- and 6-carboxylic acid esters of steroid 24-aldehydes. Examples of such esters are given as follows:

Compound XIV

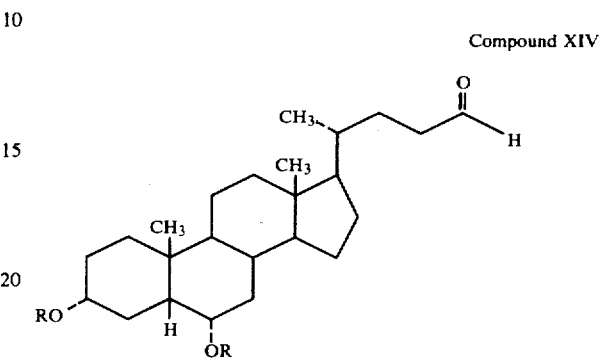

Compound XV

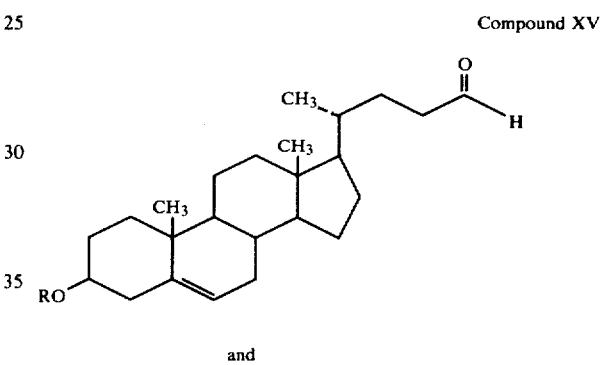

and

Compound XVI

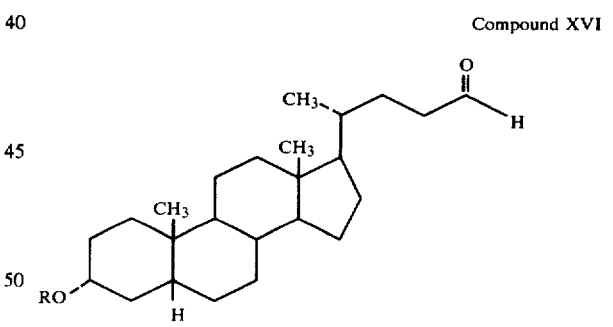

Each of the 24-carbon-24-aldehyde steroids are derivatives of hyodeoxycholic or lithocholic acid; and the term "derivative", as used herein, means any compound to which a starting compound has been converted by a chemical reaction or a series of chemical reactions.

Each of the 24-carbon steroid-24-aldehydes above described may be transformed with the Wittig reagent (ylid derived from the trimethylphosphonium ion, page 3 of my application Ser. No. 278,838) into cholest-24-ene derivatives. The side chains of all the cholestene compounds are identical as illustrated by the following structure:

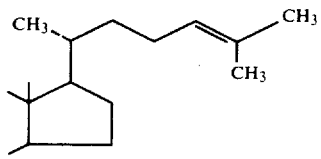

The 24-carbon steroid-24-aldehyde, Compound VIIIa, which is designated as Compound II in my application Ser. No. 278,838, may be selected for conversion to 24,25-dihydroxycholesterol. All of the other 24-carbon steroid 24-aldehydes are also useful intermediates in the synthesis of 25-hydroxycholesterol or 1α,25-dihydroxycholesterol and are precursors of the corresponding vitamin D₃ species.

Typical reactions in which selected 24 carbon steroid-24-aldehydes shown in structural form are converted to 24,25-dihydroxycholesterol will now be set forth in the following demonstrations:

Demonstration No. 1

Compound V

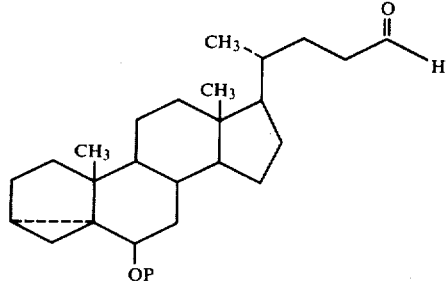

Wittig reagent
(See Serial No. 278,838, page 3.)

(See Serial No. 236,160, page 6.)

Compound XI

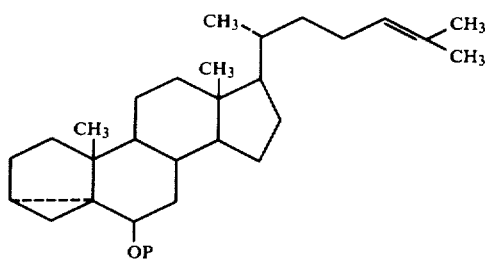

(See German Offenlegungsschrift 2,424,498, page 20.)

-continued

Demonstration No. 1

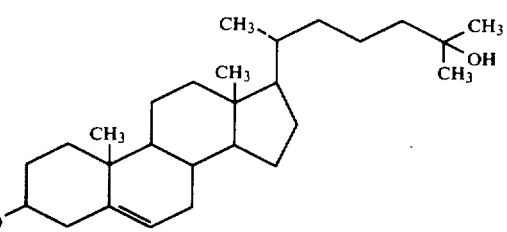

25-hydroxycholesterol

Demonstration No. 2

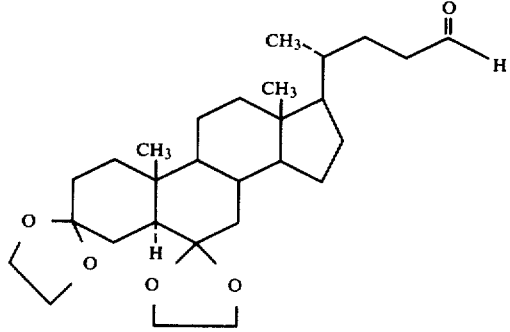

Wittig reagent (See Serial No. 278,838, page 5, step 4.)

-continued
Demonstration No. 2

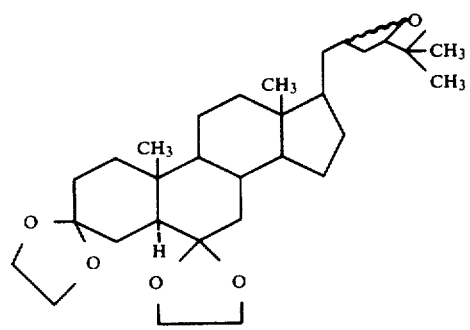

(See German Offenlegungs-
schrift No. 2,424,498,
page 21.)

↓ reduction

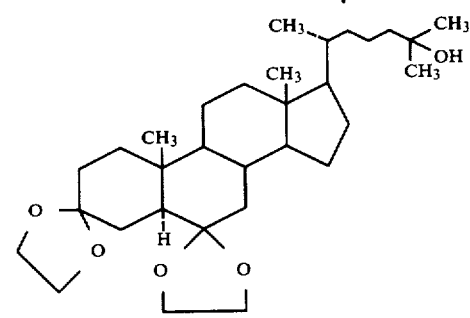

(See U.S. Pat. No.
4,163,744, page 6.)

↓ hydrolysis

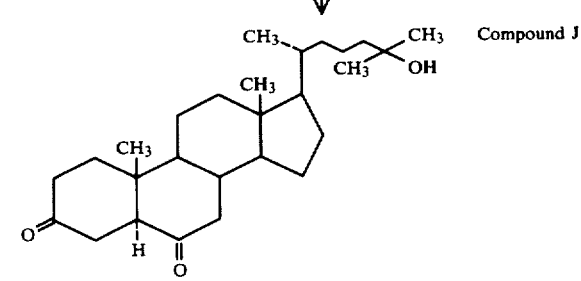   Compound J (See U.S. Pat. No.
4,163,744, page 6.)

↓

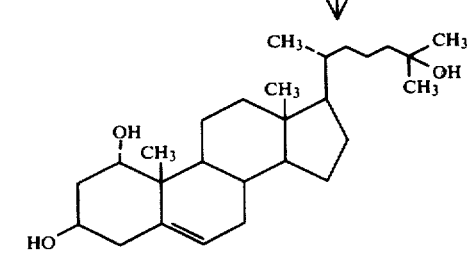

-continued
Demonstration No. 2

(See U.S. Pat. No. 1α,25-dihydroxycholesterol
4,163,744, page 6 and
reference here cited.)

Demonstration No. 3

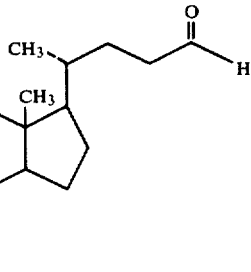

Compound VIb
(See Ser. No. 236,160, page 6)

↓ Wittig reagent

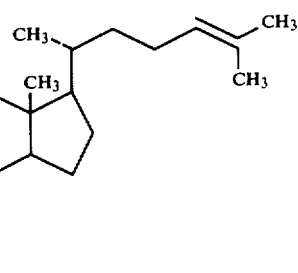

(See Ser. No. 278,838,
page 5, step 4.)

↓ epoxidation

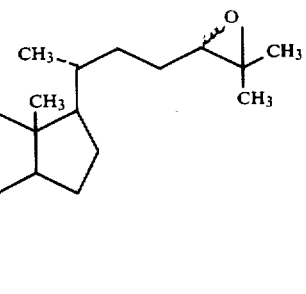

(See German Offen-
legungsschrift 2,424,498,
page 21.)

↓ reduction

-continued
Demonstration No. 3

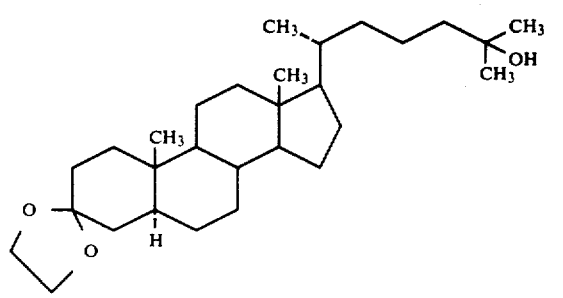

(See Ser. No. 278,838, Example 9, page 12.)

↓ hydrolysis

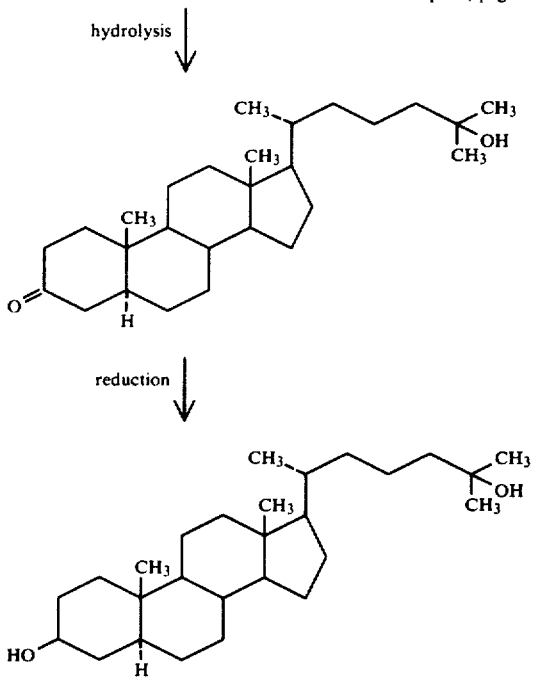

↓ reduction

↓ Introduction of the 1α-hydroxy in ring A.

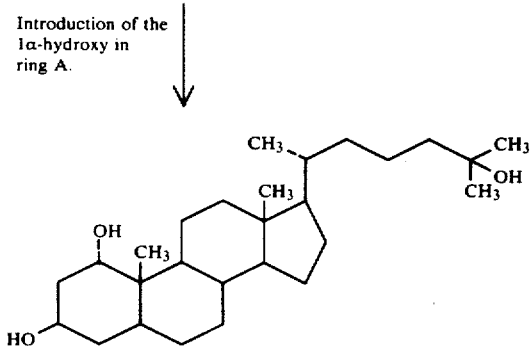

1α,25-dihydroxycholesterol
(See K. Ochi et al, Chem. Pharm. Bull. 26, 2386 [1978], Chart 1, page 2387.)

Demonstration No. 4

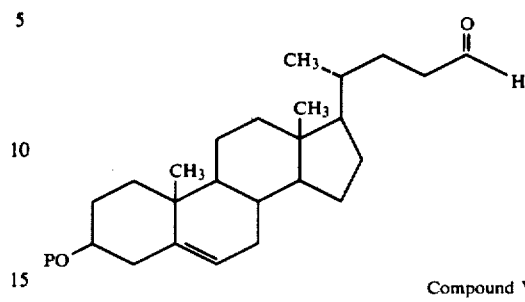

Compound VIII
(See Ser. No. 236,160, page 7.)

↓ Wittig reagent

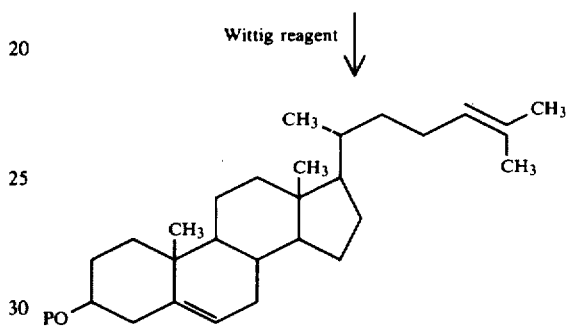

Desmesterol acetate, Compound V.

(The acetate of this compound, where P = acetyl, is Compound V of the M. Morisaki et al, Chem. Pharm. Bull. 21, [1973], page 458, which is desmosterol acetate.)

↓

25-Hydroxycholesterol acetate, Compound IX of M. Morisaki et al, Chem. Pharm. Bull. 21, page 458.

Demonstration No. 5

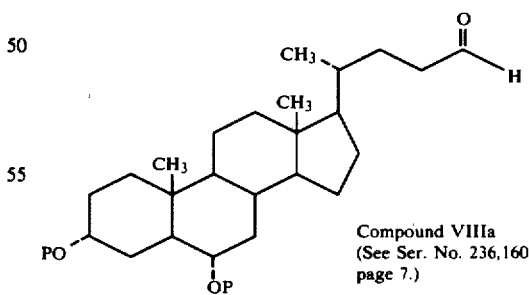

Compound VIIIa
(See Ser. No. 236,160, page 7.)

(Compound VIIa, of Ser. No. 236,160, page 7, is the starting material in my application, Ser. No. 278,838 and the conversion of this material to 24,25-dihydroxycholesterol is described in complete detail in that application.)

Demonstration No. 6

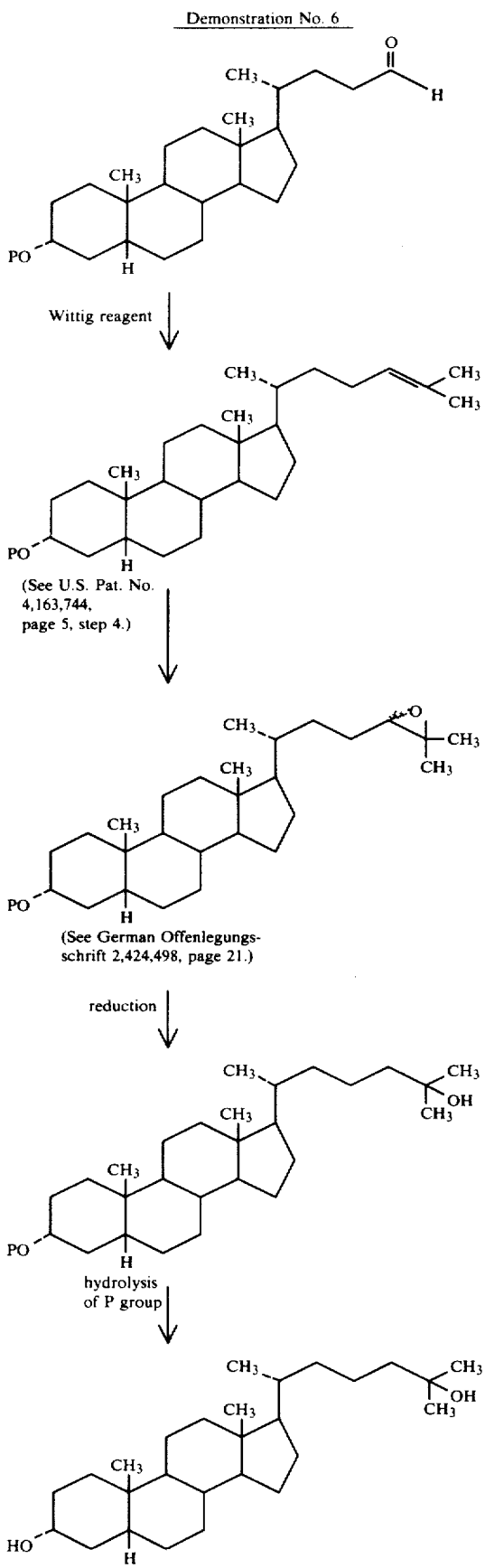

(See U.S. Pat. No. 4,163,744, page 5, step 4.)

(See German Offenlegungsschrift 2,424,498, page 21.)

reduction hydrolysis of P group

-continued
Demonstration No. 6

(See K. Ochi et al, Chem. Pharm. Bull. 26, 2386 [1978].)

1α-hydroxyl introduction into ring A

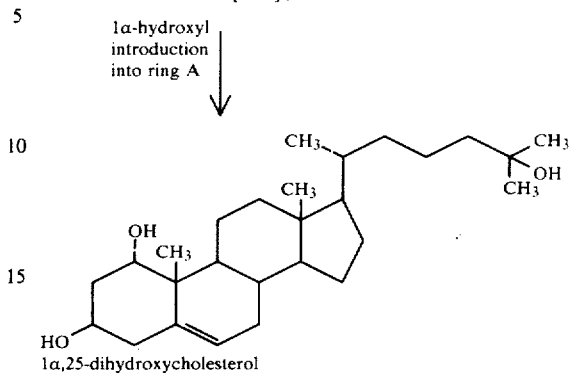

1α,25-dihydroxycholesterol

Specific examples illustrating how the processes herein described may be carried out are given as follows:

EXAMPLE 1

(Conversion of Compound IVa to VIIIa, P=2-THP)

Preparation of 3α, 6α-bis(2-tetrahydropyranyloxy)-5β-cholane-24-al by oxidation of the 24-ol with chromium trioxide-pyridine The bis-2-tetrahydropyranyl ether of methyl hyodeoxycholate is reduced with an alkaline reducing agent, such as Vitride-T, to the 3α,6α-bis(2-tetrahydropyranyloxy)-5-cholane-24-ol, as described in U.S. Pat. No. 4,217,279. To a solution of 19.3 ml of pyridine and 12.0 g of chromium trioxide in 300 ml of methylene chloride (prepared under the safety precautions recommended by Org. Synthesis, Vol. 55, 84 (1976)), a solution of 11 g of 3α,6α-bis(2-tetrahydropyranyloxy)-5-cholan-24-ol in 40 ml of methylene chloride is added dropwise in 8 minutes. Stirring is continued for 20 more minutes. During the reaction, the wall of the vessel becomes covered with a black substance, which is then scraped off and removed by filtration. The filtrate is evaporated under reduced pressure to dryness, and the residue is extracted with 400 ml of ether. The ether extract is washed twice with a saturated sodium chloride solution dried over anhydrous magnesium sulfate and evaporated. The residue was identified by IR and NMR as the 3α,6α-bis(2-tetrahydropyranyloxy)-5-cholane-24-aldehyde.

NMR (CDCl$_3$): δ9.76

(t, 1.95 Hz, $-\overset{\overset{O}{\|}}{C}-H$);

3.52, 3.87, 4.69 (m, THP); 3.52, 3.87 (m, 3/6-H); 0.92 (d, 4.6 Hz, C-21-CH$_3$); 0.89 (s, C-19-CH$_3$); 0.63 (s, C-18-CH$_3$).

EXAMPLE 2

(Conversion of Compound IVa to VIIIb, P=2-THP)

Preparation of 3α-(2-tetrahydropyranyloxy)-5β-cholane-24-al by oxidation of the 24-ol with chromium trioxide-pyridine The 2-tetrahydropyranyl ether of methyl lithocholate is reduced to the 3α-(2-tetrahydropyranyloxy)-24-ol and is oxidized with chromium trioxide-pyridine to the 3α-(2-tetrahydropyranyloxy)-cholane-24-aldehyde, as in Example 1.

EXAMPLE 3

(Conversion of IVa→VIIIa, P=t-butyl; IVb→VIIIb, P=t-butyl)

Preparation of 3α,6α-bis(t-butyloxy)-5β-cholane-24-al and 3α-(t-butyloxy)-5β-cholane-24-al by oxidation of the corresponding 24-ols with chromium trioxide-pyridine Methyl hyodeoxycholate (12.32 g) is dissolved in 300 ml of methylene chloride, 3 ml of sulfuric acid is added, and isobutylene is bubbled through the solution. The flask then is kept closed overnight. The methylene chloride solution is washed with 5% aqueous bicarbonate, dried and evaporated. The residue, 3α,6α-bis(t-butyloxy) methyl cholanate is reduced in toluene solution with an alkaline reducing agent, such as Vitride, to give 3α,6α-bis(t-butyloxy)-5β-cholane-24-ol. The 24-alcohol group then is oxidized with chromium trioxide-pyridine, as in Example 1, to the 3α,6α-bis(t-butyloxy)-5β-cholane-24-aldehyde.

In the same manner, 3α-(t-butyloxy)-5β-cholane-24-aldehyde is prepared from methyl lithocholate.

EXAMPLE 4

(Conversion of IVa→VIIIa, P=trimethylsilyl; IVb→VIIIb, P=trimethylsilyl)

Preparation of 3α,6α-bis(trimethylsilyloxy)-5β-cholane-24-al and 3α-trimethylsilyloxy-5β-cholane-24-al by oxidation of the corresponding 24-ols with chromium trioxide-pyridine In diglyme solution methyl hyodeoxycholate, trimethylsilyl chloride and triethylamine are stirred for one hour. Then methylene chloride is added, the solution washed with saturated aqueous sodium chloride, dried and evaporated. The residue is dissolved in toluene and reduced with Vitride to the 3α,6α-bis(trimethylsilyloxy)-5β-cholane-24-ol which is oxidized to the 3α,6α-bis(trimethylsilyloxy)-5β-cholane-24-aldehyde with chromium trioxide-pyridine.

In the same manner, 3α-trimethylsilyloxy-5β-cholane-24-al is prepared from methyl lithocholate.

EXAMPLE 5

(Conversion of IVa→VIIIa, P=t-butyl dimethylsilyloxy; IVb→VIIIb, P=t-butyl dimethylsilyloxy)

Preparation of 3α,6α-bis(t-butyl dimethylsilyloxy)-5β-cholane-24-al and 3α-(t-butyl dimethylsilyloxy)-5β-cholane-24-al by oxidation of the corresponding 24-ols with chromium trioxide-pyridine Methyl hyodeoxycholate is dissolved in dimethylformamide, t-butyl dimethylsilyl imidazole is added, and the solution stirred at room temperature for five hours. The solution is concentrated under reduced pressure, methylene chloride is added, and the solution washed with saturated aqueous sodium chloride. The methylene chloride solution is dried, evaporated to dryness, the residue dissolved in toluene and reduced to the 24-alcohol with Vitride. The 24-alcohol group is then oxidized with chromium trioxide-pyridine to the 3α,6α-bis(t-butyl dimethylsilyloxy)-5β-cholane-24-aldehyde.

In the same manner, 3α-t-butyl dimethylsilyloxy-5β-cholane-24-al is prepared from methyl lithocholate.

EXAMPLE 6

(Conversion of Compound I to Compound V)

Preparation of 3α5-cyclo-6β-methoxycholane-24-al by oxidation of the 24-al with chromium trioxide-pyridine 3α,5-Cyclo-6β-methoxycholane-24, prepared according to U.S. Pat. No. 4,134,904, is dissolved in methylene chloride and oxidized with chromium trioxide-pyridine to the 3α,5-cyclo-6β-methoxycholane-24-aldehyde.

EXAMPLE 7

(Conversion of IVa→VIIIa, P=β-methoxyethoxymethyl; IVb→VIIIb, P=β-methoxyethoxymethyl)

Preparation of 3α,6α-bis(β-methoxyethoxymethoxy)-5β-cholane-24-ol and 3α-(β-methoxyethoxymethoxy)-5β-cholane-24-al by oxidation of the corresponding 24-ols with chromium trioxide-pyridine 3α,6α-Bis(β-methoxyethoxymethoxy)-5β-cholane-24-ol is dissolved in methylene chloride and oxidized with chromium trioxide-pyridine to 3α,6α-bis(β-methoxyethoxymethoxy)-5β-cholane-24-aldehyde.

Methyl lithocholate is dissolved in methylene chloride, and β-methoxyethoxymethyl chloride and diisopropylethylamine are added. The mixture is stirred for four hours, ether added and washed with water. After drying the solvents are evaporated, the residue dissolved in toluene and the 24-ester group reduced to the 24-alcohol group with Vitride. The 24-alcohol then is oxidized with chromium trioxide-pyridine and the 3α-(β-methoxyethoxymethoxy)-5β-cholane-24-aldehyde obtained.

EXAMPLE 8

(Conversion of IIa→VIa, P=diethylene ketal; IIb→VIb, P=diethylene ketal)

Preparation of 3,6-dioxo diethylene ketal-5α-cholane-24-al and of 3-oxo diethylene ketal-5α-cholane-24-al by oxidation of the corresponding 24-ols with chromium trioxide-pyridine 3,6-Dioxo diethylene ketal-5α-cholane-24-ol, prepared according to Example 3, U.S. Pat. No. 4,163,744, is dissolved in methylene chloride and oxidized with chromium trioxide-pyridine to the 3,6-dioxo diethylene ketal-5α-cholane-24-aldehyde in the same manner as any of the 3- and/or 6-protected 24-alcohols of Examples 1–7 are oxidized.

Methyl 3-keto-5α-cholanate, obtained by oxidation of methyl lithocholate, is refluxed in benzene solution with ethylene glycol and catalytic amounts of p-toluenesulfonic acid as described in Example 2, U.S. Pat. No. 4,163,744. The methyl 3-oxo diethylene ketal-5α-cholanate is reduced to the 24-alcohol in the same manner as described in Example 3, U.S. Pat. No. 4,163,744; and the 3-oxo diethylene ketal-5α-cholane-24-ol oxidized to the 3-oxo diethylene ketal-5α-cholane-24-aldehyde with chromium trioxide-pyridine in the same manner as any of the 3- and/or 6-protected 24-alcohols of Examples 1–7 are oxidized.

EXAMPLE 9

Oxidation to 24-aldehydes of the 24-alcohols by the sulfoxidecarbodiimide reaction Any of the 24-alcohols, oxidized to 24-aldehydes with chromium trioxide-pyridine, can also be oxidized to the same aldehydes by the sulfoxide-carbodiimide reaction. The procedure is as follows:

The protected steroid 24-alcohol (0.03 mole) is dissolved in 5 ml of dimethylsulfoxide and 1.85 g of dicyclohexylcarbodiimide and a solution of 0.24 ml of pyridine and 0.12 ml of trifluoroacetic acid in 10 ml of benzene are added. After standing overnight 25 ml ethyl acetate is added, dicyclohexylurea is removed by filtration, the filtrate washed with a 1/10 N sodium hydroxide solution and then with water. After drying, the solvents are evaporated, and the residue dissolved in benzene. By chromatography through a silica column, first a small amount of a by-product, an O-(thiomethoxymethyl)-derivative of the 24-alcohol (1–2%) passes through the column, followed by the 24-aldehyde derivative (70–80% yields). The 24-aldehydes are identical in their IR and NMR spectra with the ones obtained by the chromium trioxide-pyridine oxidations.

EXAMPLE 10

Oxidation to 24-aldehydes of the 24-alcohols with aluminum isopropoxide and cyclohexanone Any of the 24-alcohols oxidized to 24-aldehydes with chromium trioxide-pyridine, or by the sulfoxide-carbodiimide reaction, can also be oxidized to the same aldehydes with the Oppenauer procedure. The procedure is as follows:

The protected steroid alcohol (0.01 mole) is dissolved in 100 ml of toluene and 30 ml of cyclohexanone is added. Traces of moisture are removed by distillation; then 2 g of aluminum isopropoxide is added, and the solution is refluxed for 3 hours. After cooling, the solution is extracted with 0.1 N sodium hydroxide solution, then washed with water, dried and the solvents evaporated. The residue contains, as determined by IR and NMR spectral measurements, the same 24-aldehyde as is obtained by chromium trioxidepyridine oxidation or by the sulfoxide-carbodiimide reaction, as described in Examples 1–9.

EXAMPLE 11

Removal of acid labile protecting groups from hydroxyl groups in ethanol-water p-Toluenesulfonic acid (2.6 g) and 50 mmoles of one of the steroid aldehydes with 2-tetrahydropyranyl, 3α,5-cyclosteroid, t-butyl, trimethylsilyl or t-butyl dimethylsilyl hydroxyl protection in the 3- and 6-positions of the nucleus are refluxed in a mixture of 550 ml of ethanol and 160 ml of water for one hour. The solution is cooled, neutralized with aqueous ammonia and extracted with hexane. The hexane layer is dried and evaporated under reduced pressure. The residue of the hexane extract, as shown from IR and NMR spectral data, is, according to the structure of the starting material, the corresponding steroid 24-aldehyde, Compound IX or Compound XIa or Compound IXb.

EXAMPLE 12

Removal of acid labile protecting groups from hydroxyl groups in dioxane-water

The same protecting groups, as listed in Example 11, are removed in the same manner, as in Example 11, when the solvent consists of a mixture of 400 ml of dioxane and 200 ml of water.

EXAMPLE 13

(Removal of β-methoxyethoxymethyl protecting group; conversion of V→IX; VII→IX; VIIIa→XIa; VIIIb→XIb)

Removal of the β-methoxyethoxymethyl protecting group

After dissolving 30 mmoles of one of the steroid 24-aldehydes with β-methoxyethoxymethyl protection on the 3- and 6-hydroxyl groups in 40 ml of methylene chloride, 0.6 ml of methanol is added. To this solution 2.25 g of zinc bromide is added, and the mixture is stirred overnight. Unreacted zinc bromide is removed by filtration and the filtrate diluted with ether. After washing with water, the organic layer was dried and evaporated. The same steroid structures, as in Examples 11 and 12, as shown from IR and NMR spectra data, are obtained by the removal of the β-methoxyethoxymethyl ether protecting group.

EXAMPLE 14

(Conversion of VIa→Xa; VIb→Xb)

After dissolving 15 mmole of one of the steroid 24-aldehydes, having diethylene ketal protection on the 3- and 6-ketone group, in 130 ml of ethanol containing 6 ml of water, 6 ml of concentrated sulfuric acid is added and the mixture refluxed for one hour. The reaction mixture is cooled and poured into 1.4 liter of ice water. The product is removed by extraction with methylene chloride, the solution dried and evaporated. The residue contains, as shown from IR and NMR spectral data, the respective steroid 24-aldehyde structures:

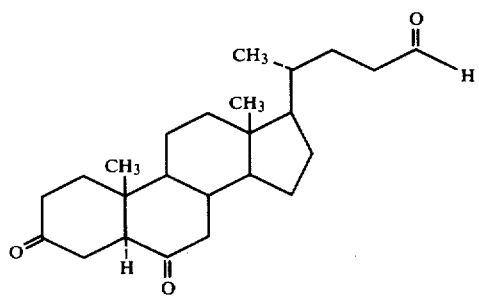

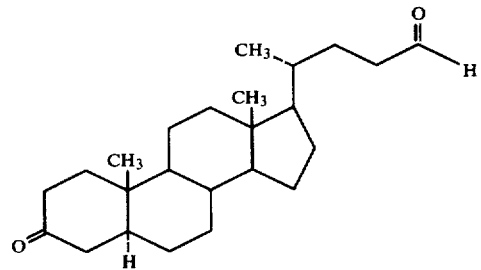

EXAMPLE 15

(Conversion of Compound XI to Compound XIV)

Preparation of 3α,6α-bis(acetyloxy)-5α-cholane-24-al

One gram of 3α,6α-bis(hydroxy)-5α-cholane-24-al is heated at reflux with 5 ml of acetic anhydride for 30 minutes. After cooling, a mixture of ice and water is added with stirring. The mixture is then extracted with methylene chloride, the organic layer washed with water, dried and evaporated to dryness. The residue is the 3α,6α-bis(acetyloxy)-5α-cholane-24-al.

EXAMPLE 16

Preparation of 3α,6α-bis(benzoyloxy)-5α-cholane-24-al

One gram of 3α,6α-bis(hydroxy)-5α-cholane-24-al is dissolved in 5 ml of pyridine. With external cooling, 1 ml of benzoyl chloride is added dropwise with stirring. The mixture is kept at room temperature for five hours, then stirred with ice water. By extraction with methylene chloride, the reaction product is removed. The methylene chloride solution is repeatedly washed with dilute hydrochloric acid, then with water. After drying, the solvent is evaporated. The residue is 3α,6α-bis(benzoyloxy)-5α-cholane-24-al.

While only certain embodiments of my invention are disclosed in detail, it will be apparent to those skilled in the art that many embodiments may be practiced and many changes may be made, all within the spirit of the invention and the scope of the appended claims.

What I claim is:

1. A 24-carbon-24-aldehyde steroid derivative of hyodeoxycholic or lithocholic acid.

2. A steroid as set forth in claim 1 having a protective group at the 3 and/or 6 positions.

3. A steroid as set forth in claim 2 in which said protecting group is 2-THP, β-MEM, t-Boc, Me₃Si or t-BuMe₂Si.

4. A steroid 24-aldehyde having the structure:

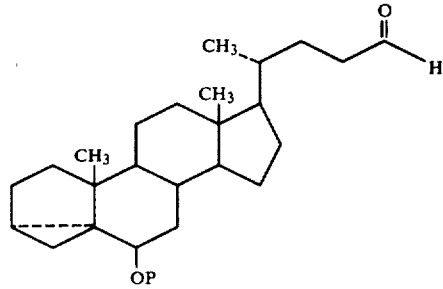

in which P is an aliphatic group.

5. A steroid 24-aldehyde having the structure:

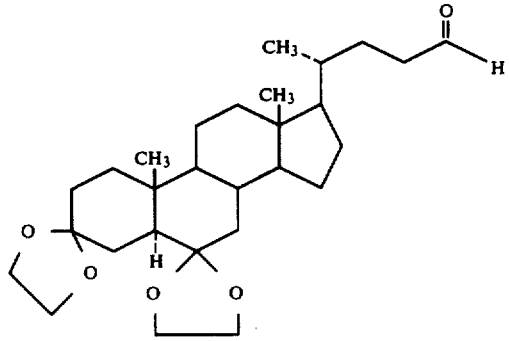

6. A steroid 24-aldehyde having the structure:

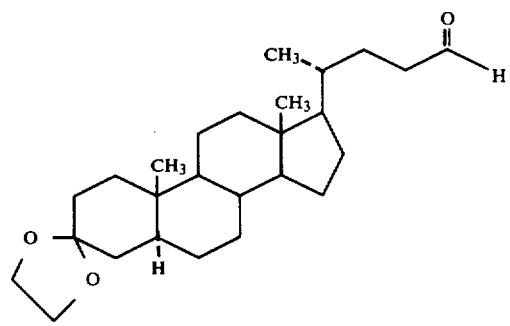

7. A steroid 24-aldehyde having the structure:

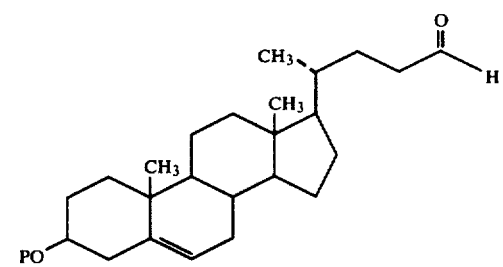

in which P is 2-tetrahydropyranyl, t-butyloxycarbonyl, trimethylsilyl, or dimethyl-t-butylsilyl.

8. A steroid 24-aldehyde having the structure:

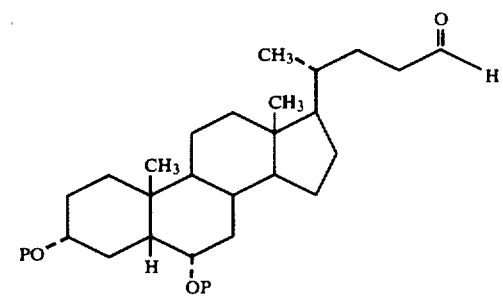

in which P is 2-tetrahydropyranyl, t-butyloxycarbonyl, trimethylsilyl or dimethyl-t-butylsilyl.

9. A steroid 24-aldehyde having the structure:

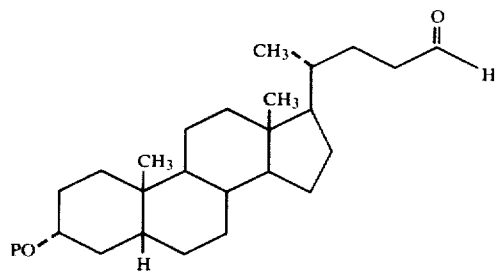

in which P is tetrahydropyranyl, t-butyloxycarbonyl, trimethylsilyl or dimethyl-t-butylsilyl.

10. A steroid 24-aldehyde having the structure:

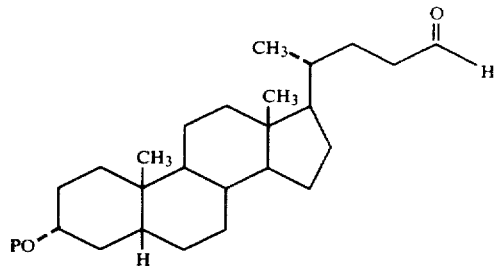

in which P is β-methoxyethoxymethyl.

11. A steroid 24-aldehyde having the structure:

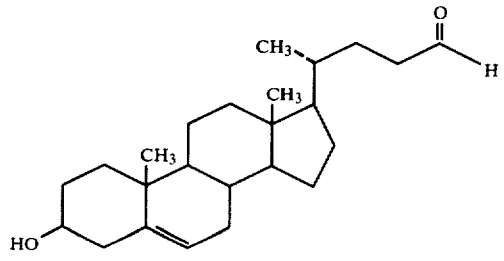

12. A steroid 24-aldehyde having the structure:

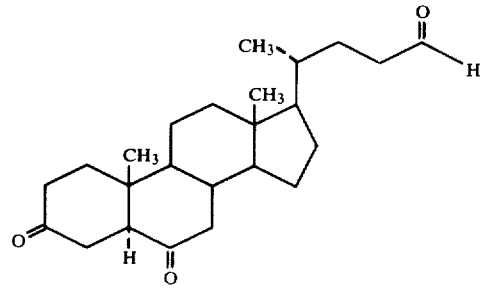

13. A steroid 24-aldehyde having the structure:

14. A steroid 24-aldehyde having the structure:

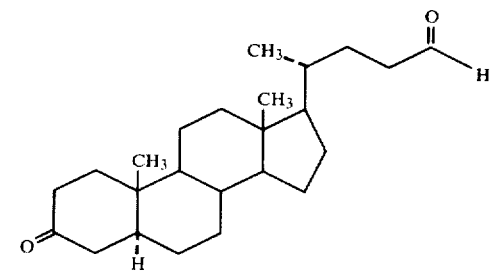

15. A steroid 24-aldehyde having the structure:

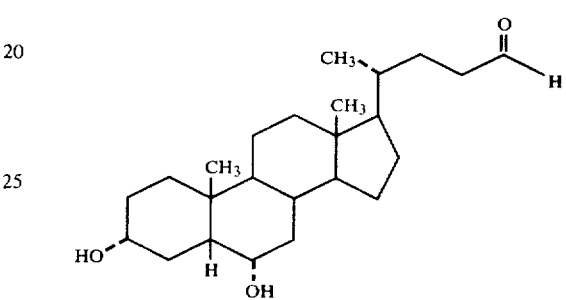

16. A steroid 24-aldehyde having the structure:

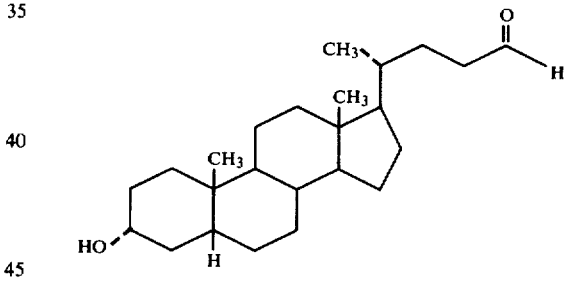

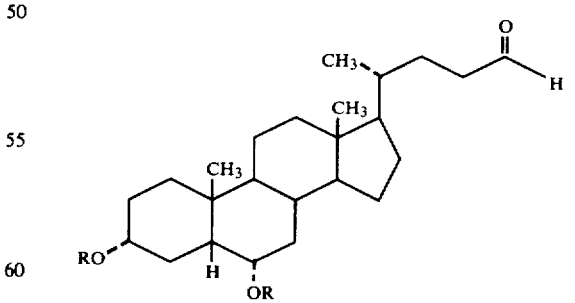

in which R is an aliphatic acyl or aromatic acyl group.

17. In a process for preparing a steroid 24-aldehyde, the step of mixing a steroid 24-alcohol having the following structure:

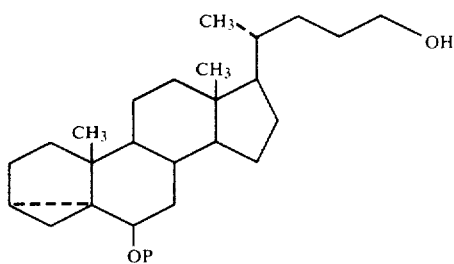

where P is methyl, in methylene chloride with a chromium trioxide-pyridine complex, for a period until reaction is complete, to prepare a steroid having the structure:

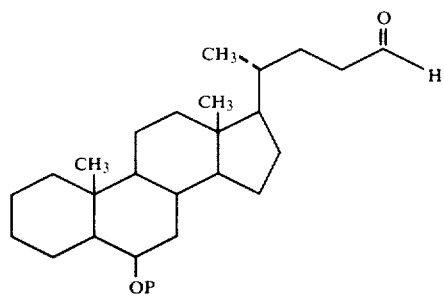

where P is methyl.

18. In a process of preparing a steroid 24-aldehyde, the step of mixing a steroid 24-alcohol having the structure:

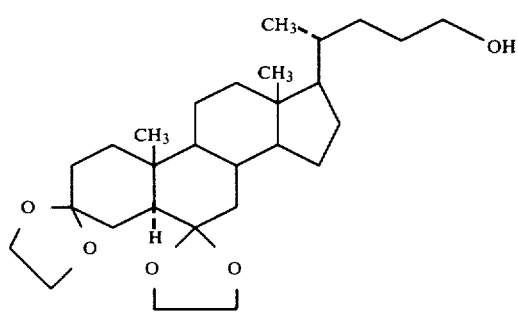

in methylene chloride with a chromium trioxide-pyridine complex for a period until reaction is complete to prepare a steroid alcohol having the structure:

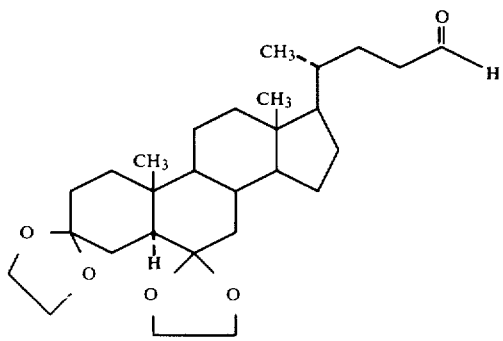

19. In a process of preparing a steroid 24-aldehyde, the step of mixing a 24-steroid alcohol having the structure:

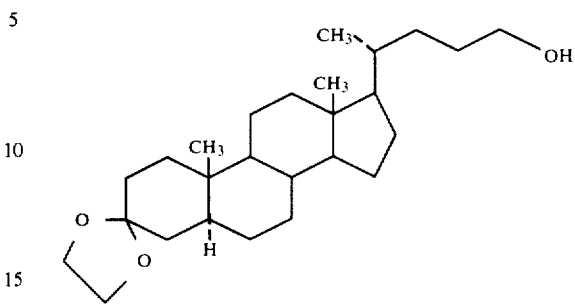

in methylene chloride with a chromium trioxide-pyridine complex for a period of time until the reaction is complete to prepare a steroid 24-alcohol having the structure:

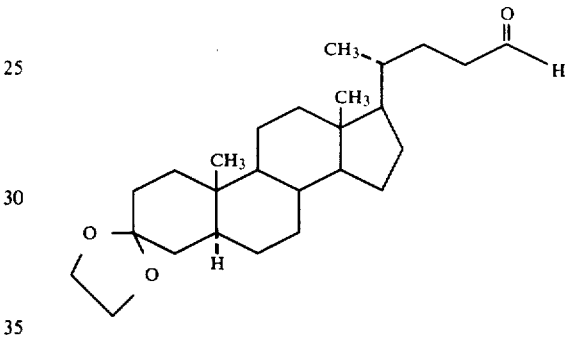

20. In a process for preparing a steroid 24-aldehyde, the step of mixing a steroid alcohol having the structure:

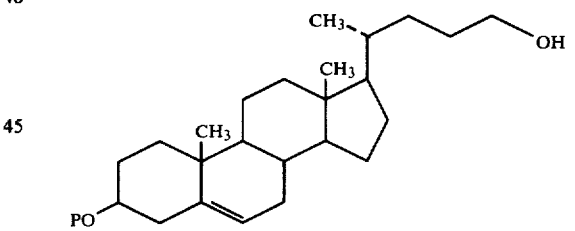

in which P is 2-tetrahydropyranyl, β-methoxyethoxymethyl, t-butyloxycarbonyl, trimethylsilyl, or dimethyl t-butylsilyl, in methylene chloride with a chromium trioxide-pyridine complex for a period of time until the reaction is complete to prepare a steroid alcohol having the structure:

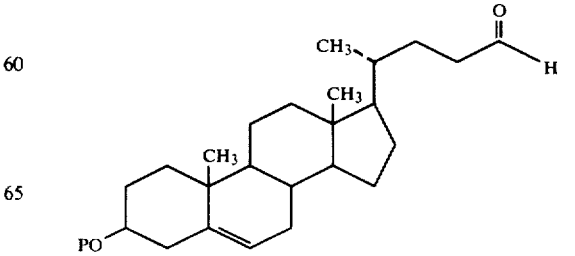

21. In a process for preparing a steroid 24-aldehyde the step of mixing a steroid alcohol having the structure:

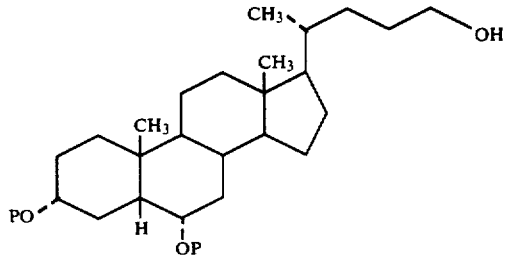

in which P is 2-tetrahydropyranyl, β-methoxyethoxymethyl, t-butyloxycarbonyl, trimethylsilyl, or dimethyl t-butylsilyl, in methylene chloride with a chromium trioxide-pyridine complex for a period of time until the reaction is complete to prepare a steroid alcohol having the structure:

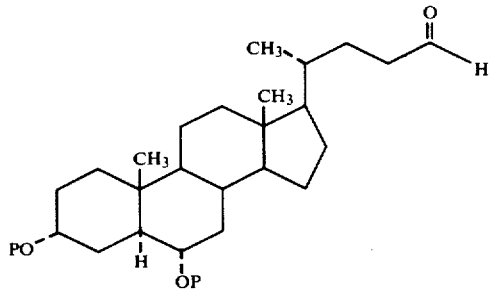

22. In a process for preparing a steroid 24-aldehyde, the step of mixing a steroid alcohol having the structure:

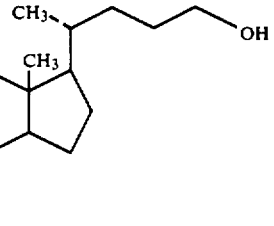

in which P is 2-tetrahydropyranyl, β-methoxyethoxymethyl, t-butyloxycarbonyl, trimethylsilyl, or dimethyl t-butylsilyl, in methylene chloride with a chromium trioxide-pyridine complex for a period of time until the reaction is complete to prepare a steroid aldehyde having the structure:

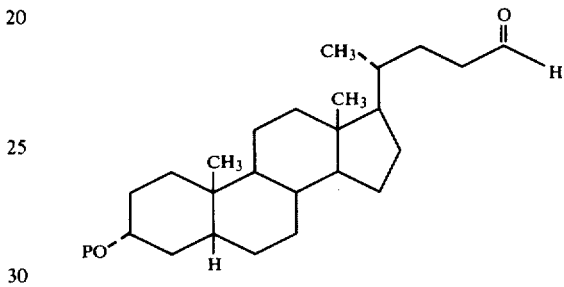

23. In a process for preparing a steroid 24-aldehyde, the step of mixing a steroid 24-alcohol with protected substituents in the 3- and 6-positions of their steroid rings with dicyclohexylcarbodiimide in dimethylsulfoxide solution in the presence of pyridine and trifluoroacetic acid until the reaction of transforming the 24-alcohol to the 24-aldehyde is completed.

24. In a process for preparing a steroid 24-aldehyde, the step of refluxing a steroid 24-alcohol with protected substituents in the 3- and 6-positions in toluene solution containing cyclohexanone and aluminum isopropoxide, until the transformation of the 24-alcohol to the 24-aldehyde is completed.

* * * * *